(12) United States Patent
Suzuki et al.

(10) Patent No.: US 10,466,237 B2
(45) Date of Patent: Nov. 5, 2019

(54) METHOD FOR EXCLUDING PROZONE PHENOMENON IN IMMUNOLOGICAL MEASUREMENT REAGENT

(71) Applicant: TANAKA KIKINZOKU KOGYO K.K., Tokyo (JP)

(72) Inventors: Keita Suzuki, Kanagawa (JP); Hisahiko Iwamoto, Kanagawa (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 184 days.

(21) Appl. No.: 15/315,822

(22) PCT Filed: Jun. 4, 2015

(86) PCT No.: PCT/JP2015/066268
§ 371 (c)(1),
(2) Date: Dec. 2, 2016

(87) PCT Pub. No.: WO2015/186812
PCT Pub. Date: Dec. 10, 2015

(65) Prior Publication Data
US 2017/0131274 A1    May 11, 2017

(30) Foreign Application Priority Data
Jun. 4, 2014  (JP) .................. 2014-116036

(51) Int. Cl.
*G01N 33/543*    (2006.01)
*G01N 33/553*    (2006.01)
*G01N 33/74*    (2006.01)
*G01N 33/558*    (2006.01)

(52) U.S. Cl.
CPC .  *G01N 33/54386* (2013.01); *G01N 33/54393* (2013.01); *G01N 33/553* (2013.01); *G01N 33/558* (2013.01); *G01N 33/74* (2013.01)

(58) Field of Classification Search
CPC ................... G01N 33/54393; G01N 33/558
See application file for complete search history.

(56) References Cited

U.S. PATENT DOCUMENTS

| 4,435,504 A | * | 3/1984 | Zuk ...................... G01N 33/558 |
|---|---|---|---|
| | | | 210/658 |
| 4,959,324 A | * | 9/1990 | Ramel .................. B01L 3/5023 |
| | | | 422/408 |

(Continued)

FOREIGN PATENT DOCUMENTS

| CN | 1580777 A | 2/2005 |
|---|---|---|
| CN | 101315382 A | 12/2008 |

(Continued)

OTHER PUBLICATIONS

CN, Office Action for Chinese application No. 201580029641.2, dated Sep. 19, 2017.

(Continued)

*Primary Examiner* — Rebecca L Martinez
(74) *Attorney, Agent, or Firm* — Orrick, Herrington & Sutcliffe LLP; Joseph A. Calvaruso; K. Patrick Herman

(57) ABSTRACT

An object is to provide an immunochromatography detection method and an immunochromatography kit in which a prozone phenomenon occurring in a sandwich method when using an analyte in which an antigen is present in a large excess amount is suppressed/excluded. The object was achieved by retaining a nonionic and hydrophilic surfactant having an HLB value of 13 to 18 in a sample addition part of an immunochromatography device, and also using a membrane having a fast flow speed as a membrane to be used for a chromatograph medium.

5 Claims, 1 Drawing Sheet

(56) References Cited

U.S. PATENT DOCUMENTS

| | | | | |
|---|---|---|---|---|
| 5,458,852 A | * | 10/1995 | Buechler | B01J 19/0093 422/417 |
| 5,739,041 A | * | 4/1998 | Nazareth | B01L 3/5023 422/423 |
| 5,871,905 A | * | 2/1999 | Thieme | G01N 33/54313 435/5 |
| 2002/0172937 A1 | * | 11/2002 | Dave | G01N 33/56905 435/5 |
| 2006/0148096 A1 | * | 7/2006 | Jina | G01N 33/558 436/514 |
| 2009/0123910 A1 | * | 5/2009 | Malick | C07K 1/145 435/5 |
| 2009/0253119 A1 | * | 10/2009 | Zhou | G01N 33/558 435/5 |
| 2010/0267049 A1 | | 10/2010 | Rutter et al. | |
| 2011/0076781 A1 | | 3/2011 | Liu et al. | |
| 2013/0011932 A1 | * | 1/2013 | Itoh | G01N 33/54393 436/501 |
| 2013/0171740 A1 | * | 7/2013 | Sakakibara | C12Q 1/6804 436/501 |
| 2014/0170187 A1 | * | 6/2014 | Settembre | A61K 39/12 424/233.1 |
| 2015/0118675 A1 | | 4/2015 | Itoh | |

FOREIGN PATENT DOCUMENTS

| | | |
|---|---|---|
| CN | 101952722 A | 1/2011 |
| CN | 102482702 A | 5/2012 |
| CN | 102713625 A | 10/2012 |
| CN | 103616514 A | 3/2014 |
| EP | 2251690 A1 | 11/2010 |
| EP | 2523001 A1 | 11/2012 |
| EP | 2829879 A1 | 1/2015 |
| JP | H10-185921 | 7/1998 |
| JP | 2004-085425 A | 3/2004 |
| JP | 2011-141252 A | 7/2011 |
| JP | 2012-524277 A | 10/2012 |
| JP | 2013-195403 A | 9/2013 |
| JP | 2014-167439 A | 9/2014 |
| WO | WO 2010-120951 A1 | 10/2010 |
| WO | WO 2012-105612 A1 | 8/2012 |

OTHER PUBLICATIONS

Wong et al, "Drug of Abuse Body Fluid Testing", Humana Press, Dec. 31, 2005, 76 page (Explanation of the book), ISBN 978-1-59259-951-6.

* cited by examiner

[FIG. 1]
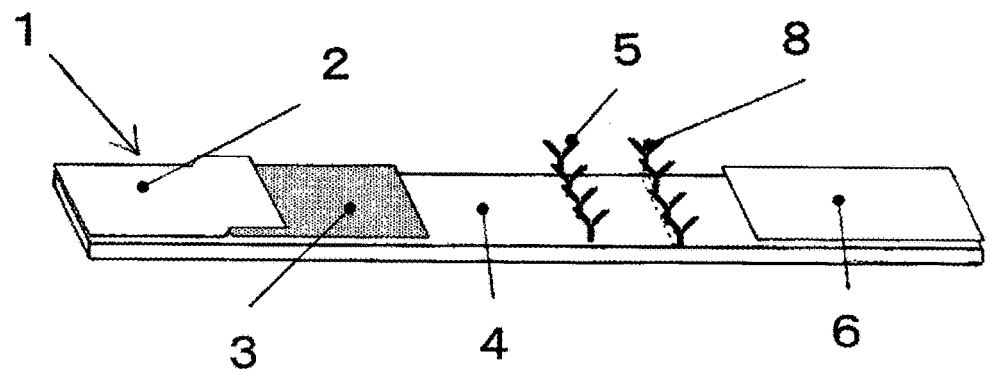
[FIG. 2]
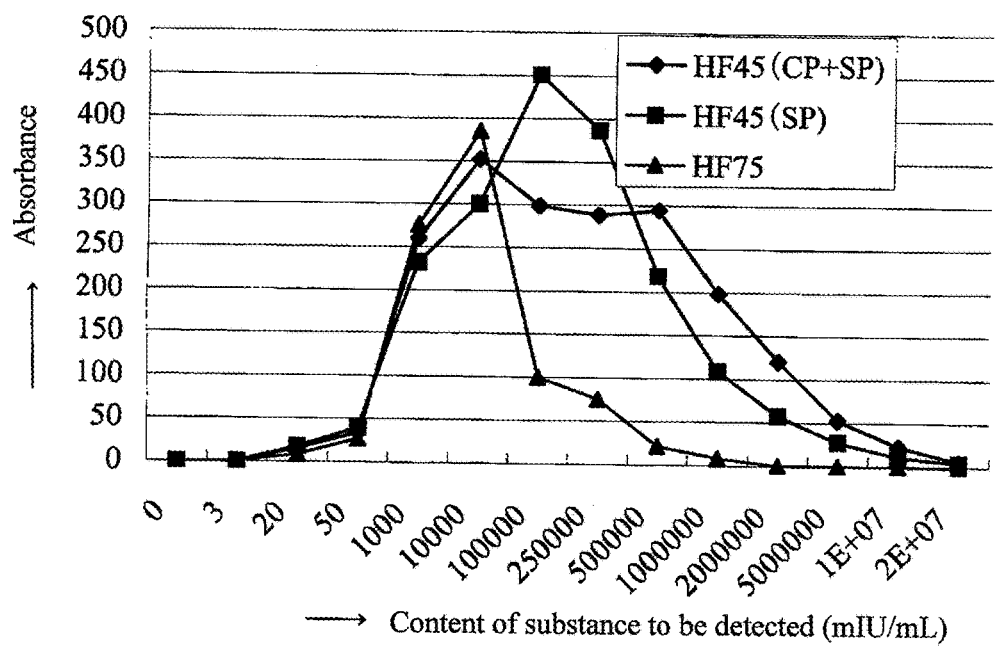

METHOD FOR EXCLUDING PROZONE PHENOMENON IN IMMUNOLOGICAL MEASUREMENT REAGENT

TECHNICAL FIELD

The present invention relates to an immunochromatography kit which is highly important as an in vitro diagnostic kit or a portable diagnostic device for rapidly, simply, and accurately detecting a substance to be detected (an antigen or the like) in a test sample in which the substance to be detected (the antigen or the like) is present in a large excess amount by utilizing an immunological antigen-antibody reaction, and also relates to a reagent composition or a detection method to be used for the kit.

The present invention particularly relates to a test method in which the test efficiency and the test accuracy are improved by excluding a prozone phenomenon occurring when a substance to be detected (an antigen or the like) in a test sample in which the substance to be detected (the antigen or the like) is present in a large excess amount, for example, a test sample such as urine or blood is detected, and a diagnostic kit to be used for the method.

BACKGROUND ART

Recently, an immunoassay of a strip type for immunochromatography has increased its versatility as a simple in vitro diagnostic kit or portable diagnostic device for detecting a substance to be detected (an antigen or the like) in a sample liquid by utilizing the specific reactivity of an antibody.

Incidentally, in an immunochromatography detection method for detecting a substance to be detected (an antigen or the like) by sandwiching the substance by an antibody, in the case where the substance to be detected (the antigen or the like) is present in a test sample in a large excess amount, a problem that a false-negative phenomenon (also referred to as "prozone phenomenon" or "high-dose hook effect") occurs as if apparently, the substance to be detected is present in a small amount or is not present at all, and not only is the S/N ratio at the time of detection decreased, but also an erroneous test result is caused has been well known, and studies have been made for excluding this prozone phenomenon.

In order to solve this problem, in an immunochromatography method utilizing an affinity chromatography principle, a sandwich method in which a substance to be detected (an antigen or the like) is sandwiched by an antibody to the substance and an antibody bound to a fine particle and detected, a method in which a substance to be detected (an antigen or the like) or an equivalent is immobilized on a chromatography support and made to compete with the substance to be detected (the antigen or the like), whereby a prozone phenomenon characteristic of the sandwich method is suppressed and the objectivity of determination is ensured, and moreover, a technique for excluding a prozone phenomenon by including a free antibody have been developed.

For example, in an immunological quantitative device, by setting a sample addition part, a labeled reactant-coated part downstream thereof, a part having a target substance (a substance to be detected) or a substance equivalent thereto immobilized thereon further downstream thereof, and a part having antibodies immobilized thereon in the form of a plurality of ladders further downstream thereof, a competitive reaction is allowed to proceed on a chromatography support, and also by providing free antibodies in the form of a plurality of ladders, a prozone phenomenon is suppressed/excluded. Then, a quantitative device which enables rapid measurement objectively in one step by making a determination based on the number of reaction lines or the coloring pattern thereof by the immobilized antibodies has been proposed (see Patent Document 1).

Further, in an affinity chromatography detection method, a method in which on a developing support, a first detection region having a substance which specifically binds to a detection target substance immobilized thereon and a second detection region having a substance which competes with the detection target substance immobilized thereon are provided, a developing solution containing a substance which is labeled with a labeling substance and specifically binds to the detection target substance and a sample is developed through these detection regions, and the detection target substance is detected based on a signal in the first and second detection regions, whereby a false-negative phenomenon is less likely to occur, and the occurrence of prozone is avoided has been proposed (see Patent Document 2).

Then, another method for excluding a prozone phenomenon, the provision of a test strip having an expanded dynamic range and a detection method using the strip have been proposed, and according to this, a prozone sample can be detected without diluting the sample.

For example, in Patent Document 3, a test strip which is a chromatography strip provided with a first end and a second end including at least a first reaction region and a second reaction region containing a capture agent which specifically binds to an analyte, and including an absorption pad in the first end, wherein the absorption pad enables the lateral flow of a sample, whereby the capture agent can bind to at least part of the analyte, and a method for detecting and measuring the presence of an analyte based on a signal of the first reaction region or from the strength of a signal from the first reaction region, the second reaction region, or a combination thereof have been proposed (see Patent Document 3).

However, the method of the related art which is an immunochromatography method in which an antibody is labeled with an insoluble support (colloidal gold particles, colored latex particles, or the like) (also referred to as "particle immunochromatography method"), and excludes a prozone phenomenon has an advantage that a quantitative determination can be achieved based on the number of reaction lines or the coloring pattern thereof for a high concentration analyte sample in which a detection target substance (an antigen or the like) is present in a large excess amount by charging free antibodies in the form of a plurality of ladders, or by providing a second or more detection regions, but has a problem that the coloration of a low concentration analyte is reduced or the free antibodies are denatured, and therefore, an effect of the measures for a prozone phenomenon is reduced over time.

Further, the method of the related art for excluding a prozone phenomenon is mainly a method capable of objectively determining/measuring a detection target substance by charging free antibodies in the form of a plurality of ladders, or by providing a second or more detection regions in addition to a standard first detection region for a detection target substance which is present in a large excess amount, and making a comprehensive determination based on these signals.

However, since there are a plurality of detection lines or there are at least two detection regions, the determination criteria are not simple but are inevitably complicated, and therefore, the method has a problem that not everyone can perform the method easily without error, and therefore, a method capable of simply making a determination has been demanded.

CITED REFERENCES

Patent Documents

Patent Document 1: JP-A-10-185921
Patent Document 2: JP-A-2004-85425
Patent Document 3: JP-T-2012-524277

DISCLOSURE OF THE INVENTION

Problems to be Solved by the Invention

An object of the present invention relates to an immunochromatography kit which is highly important as an in vitro diagnostic kit or a portable diagnostic device capable of rapidly, simply, and accurately performing detection by suppressing/excluding a prozone phenomenon in a method for detecting a substance to be detected (an antigen or the like, hereinafter also referred to as "detection target") in a test sample (also referred to as "analyte") in which the substance to be detected (the antigen or the like) is present in a large excess amount by sandwiching the substance by an antibody utilizing an immunological antigen-antibody reaction, and a reagent composition or a detection method to be used for the kit.

Further, an object of the present invention is to provide an immunochromatography device in which a prozone phenomenon occurring in a sandwich method is suppressed/excluded by using an improved member for an analyte in which an antigen is present in a large excess amount in an immunochromatography reagent.

More specifically, an object of the present invention relates to a test method in which the test efficiency and the test accuracy are improved by suppressing/excluding a prozone phenomenon occurring when a substance to be detected (an antigen or the like) in a test sample in which the substance to be detected (the antigen or the like) is present in a large excess amount, for example, in a biological sample such as urine or blood is detected, and a diagnostic kit to be used for the method.

Means for Solving the Problems

It is well known that in an immunochromatography reagent, in the case of an analyte in which an antigen is present in a large excess amount, a phenomenon (prozone phenomenon) in which the antigen which does not bind to a coloring support is captured by a test line antibody coated onto a membrane, and therefore, the test line is not colored so that a false-negative determination is made occurs.

The present inventors found for the first time that this phenomenon can be suppressed/excluded by retaining a specific nonionic surfactant in a dry state at least in a sample addition part, and using a membrane having a fast flow speed (development rate) is used as a membrane to be used for a chromatography medium.

In a detection system of the present invention, a member containing a nonionic and hydrophilic surfactant having an HLB value of 13 to 18 is used as the specific nonionic surfactant, and also the high flow rate (a time required for sucking up water by 4 cm (sec/40 mm)) of a membrane to be used for a chromatography medium is 75 (sec/40 mm) or less, thereby excluding a prozone phenomenon, and thus, an immunoassay reagent, an immunoassay method, an immunochromatography kit, and the like capable of accurately, easily, and rapidly testing an analyte in which an antigen is present in a large excess amount are provided.

The present invention provides an immunochromatography device and an immunochromatography kit, each using an immunochromatography method, and an immunochromatography detection method using the same according to the following (1) to (12).

The immunochromatography device of the present invention has features as follows.

(1) The first feature of the present invention resides in an immunochromatography device for detecting a detection target in an analayte, which includes a sample addition part, a labeling substance retaining part, a chromatography medium having a detection part, and an absorption part, wherein a nonionic and hydrophilic surfactant having an HLB value of 13 to 18 is retained at least in the sample addition part, and a membrane having a fast flow speed is used as a membrane to be used for the chromatography medium.

A detection kit (also referred to as "immunochromatography kit") using the immunological detection method of the present invention has features as follows.

(2) The second feature of the present invention resides in an immunochromatography kit for detecting a detection target in an analyte, comprising a sample addition part, a labeling substance retaining part, a chromatography medium having a detection part, and an absorption part, wherein a nonionic and hydrophilic surfactant having an HLB value of 13 to 18 is retained at least in the sample addition part, and a membrane having a fast flow speed is used as a membrane to be used for the chromatography medium.

(3) The third feature of the present invention resides in an immunochromatography kit, wherein the flow speed of the membrane is 75 or less as a high flow rate (sec/40 mm).

(4) The fourth feature of the present invention resides in an immunochromatography kit, wherein the nonionic and hydrophilic surfactant having an HLB value of 13 to 18 is retained in both of the sample addition part and the labeling substance retaining part.

(5) The fifth feature of the present invention resides in an immunochromatography kit, wherein the content of the nonionic and hydrophilic surfactant is from 0.1 to 5 µg/mm$^2$ of the unit area of the sample addition part or both of the sample addition part and the labeling substance retaining part of the immunochromatography kit.

(6) The sixth feature of the present invention resides in an immunochromatography kit, wherein a labeling substance modified with gold nanoparticles is retained in a dry state in the labeling substance retaining part.

(7) The seventh feature of the present invention resides in an immunochromatography kit, wherein the average particle diameter of the gold nanoparticles is from 20 to 60 nm.

The immunochromatography detection method of the present invention has features as follows.

(8) The eighth feature of the present invention resides in an immunochromatography detection method, comprising a step of adding an analyte to a sample addition part, a step of recognizing a detection target by a labeling substance which is modified with gold nanoparticles and is retained in a labeling substance retaining part, a step of developing a complex of the labeling substance and the detection target as a mobile phase, and a step of detecting the detection target in the developed mobile phase in a detection part, wherein a nonionic and hydrophilic surfactant having an HLB value of 13 to 18 is retained at least in the sample addition part, and a membrane having a fast flow speed is used as a membrane to be used for a chromatography medium.

(9) The ninth feature of the present invention resides in an immunochromatography detection method, wherein the average particle diameter of the gold nanoparticles is from 20 to 60 nm.

(10) The tenth feature of the present invention resides in an immunochromatography detection method, wherein the analyte is a biological sample.

(11) The eleventh feature of the present invention resides in an immunochromatography detection method, wherein the detection target is a peptide hormone.

(12) The twelfth feature of the present invention resides in an immunochromatography detection method, wherein a nonionic and hydrophilic surfactant having an HLB value of 13 to 18 is retained in both of the sample addition part and the labeling substance retaining part.

The present invention has features as described above, and therefore can achieve the above-mentioned objects.

Effect of the Invention

The present invention can significantly exclude a prozone phenomenon (a phenomenon in which a test line is not colored so that a false-negative determination is made although an antigen is present) by retaining a nonionic and hydrophilic surfactant having an HLB value of 13 to 18 at least in a sample addition part (also referred to as "sample pad") and using a membrane having a fast flow speed (development rate) as a membrane to be used for a chromatography medium in a method for detecting a substance to be detected (an antigen or the like) in a test sample (also referred to as "analyte") in which the substance to be detected (the antigen or the like) is present in a large excess amount by sandwiching the substance by an antibody utilizing an immunological antigen-antibody reaction.

Due to this, the present invention can provide an immunochromatography device and an immunochromatography kit which is highly important as an in vitro diagnostic kit or a portable diagnostic device, each capable of rapidly, simply, and accurately performing detection in a method for detecting a substance to be detected (an antigen or the like) in a test sample (also referred to as "analyte") in which the substance to be detected (the antigen or the like) is present in a large excess amount by sandwiching the substance by an antibody utilizing an immunological antigen-antibody reaction, and further the detection method.

That is, in the present invention, a substance to be detected (an antigen or the like) and a labeling substance can be promptly conjugated to each other by the action of a nonionic and hydrophilic surfactant having an HLB value of 13 to 18 which is retained in a sample addition part (also referred to as "sample pad"), or in both of a sample addition part and a labeling substance retaining part (also referred to as "conjugation pad").

Further, by using a membrane having a fast flow speed (development rate) as a membrane to be used for a chromatography medium, and moreover, by using colloidal gold having a relatively small particle diameter of 20 to 60 nm as colloidal gold to be used as a labeling substance for modifying an antibody, as a result of the synergetic action thereof, although the mechanism of action is not clear, the formation of a complex of a substance to be detected (an antigen or the like) and a labeling substance is extremely rapid, and also the migration and development of the complex in the chromatography medium is very smooth and rapid without causing any problem, and then, the complex is promptly bound to a test line antibody so that the test line can be colored.

As a result, a test agent capable of making a determination of a result accurately and rapidly with a fast development rate, simply, and with high sensitivity without causing a prozone phenomenon could be provided. For example, when LH or hCG or the like in urine to be used as an analyte is detected, the sensitivity is not decreased without increasing the amount of binding antibody and also without changing the coloring strength when the concentration of a substance to be detected (an antigen or the like) is low, and also a prozone phenomenon is significantly suppressed/excluded, and therefore, it is easy to make out the determination criteria, and thus, a determination of a test result can be accurately made.

BRIEF DESCRIPTION OF DRAWINGS

FIG. 1 is a view showing an immunochromatography device of the present invention.

FIG. 2 is a graph obtained by graphing the data in [Table 5] of the present invention.

EMBODIMENTS FOR CARRYING OUT THE INVENTION

Hereinafter, the present invention will be described in detail.

An embodiment of the present invention is based on an immunochromatography method or a detection method which applies the same in which a complex is formed by an antigen-antibody reaction in which a binding substance (an antibody) which has any of a variety of labels and specifically binds to a detection target (an antigen) which is a substance to be detected in any of a variety of analytes is reacted with the detection target on a chromatography medium, and the complex is developed in the direction of an absorption part on the immunochromatography medium, and confirmed by any of a variety of detection means. As the antibody which most specifically reacts with and binds to the antigen, for example, a monoclonal antibody and a polyclonal antibody, or another known antibody, each of which specifically binds to the antigen, can be arbitrarily used.

As the label, an enzyme, a coloring substance, a fluorescent substance, a radioactive substance, or the like can be arbitrarily used, however, the label may be determined so as to exhibit the characteristics of the immunochromatography method that the operation is simple and also the test time is short, or in consideration of the types of the antibody and the antigen.

Further, the detection means are characterized by having performance that a determination can be accurately made by visual determination in order to exhibit the characteristics of the immunochromatography method that the operation is simple and a determination can be made in a relatively short time. However, in the case where time, accuracy, etc. are demanded, it is also possible to perform detection by supplementing any of a variety of detection means such as spectrophotometric detection and radiation detection.

The best mode for carrying out the immunochromatography device, the immunochromatography kit, the immunoassay method, or the immunochromatography detection method which can be used for the immunochromatography method of the present invention will be sequentially described.

The immunochromatography device of the present invention is a device to be used in an immunoassay, and as one mode, an immunochromatography kit is included. In this immunochromatography device, a nonionic and hydrophilic surfactant having an HLB value of 13 to 18 is included and retained at least in a sample addition part (2).

However, it is also possible to include and retain the surfactant in one or more parts of a labeling substance retaining part (3) and moreover a membrane (4) which is a chromatography medium in addition thereto. In the case where this nonionic and hydrophilic surfactant is included in the sample addition part, the device has a property to perform sequential migration and development into the labeling substance retaining part (3), the chromatography medium (4), a detection part (hereinafter also referred to as "determination part") (5), and an absorption part (6).

In the immunochromatography device of the present invention, the nonionic and hydrophilic surfactant having an HLB value of 13 to 18 is included and retained in a dry state in the sample addition part (2) or in both of the sample addition part (2) and the labeling substance retaining part (3).

The specific nonionic surfactant which can be used in the present invention is a nonionic and hydrophilic surfactant having an HLB value of 13 to 18, more preferably is a nonionic and hydrophilic surfactant having an HLB value of 14 to 17.

Examples of the surfactant which can be used include commercially vailable products such as Triton X-100 (trade name), Brij 35 (trade name), Tween 20 (trade name), and NP-40 (trade name). Particularly preferred examples thereof include Brij 35 (trade name) and Tween 20 (trade name). When the HLB value is less than 13, the solubilization action is insufficient, and therefore, the sensitivity is deteriorated. On the other hand, when the HLB value exceeds 18, the solubilization action is sufficient, however, the hydrophilicity is too high, and therefore, the sensitivity is deteriorated.

It is found that in consideration also of the properties of permeation and solubilization and the like of the surfactant, a nonionic surfactant having an HLB value of about 13 to 18 is most suitable for the immunochromatography device of the present invention. The behavior of the nonionic surfactant of the present invention can exhibit the characteristic properties and performance which cannot be observed in other anionic surfactants, cationic surfactants, and amphoteric surfactants in cooperation with the high flow rate properties of the membrane of the chromatography medium and also the properties of gold nanoparticles.

The content of the nonionic and hydrophilic surfactant having an HLB value of 13 to 18 to be retained in the sample addition part (also referred to as "sample pad") or in both of the sample addition part and the labeling substance retaining part (also referred to as "conjugation pad") of the present invention is from 0.10 to 5.0 μg/mm$^2$, preferably from 0.15 to 3.0 μg/mm$^2$, particularly preferably from 0.20 to 1.0 μg/mm$^2$.

When the content is less than 0.10 μg/mm$^2$, the flow is deteriorated, and on the other hand, when the content exceeds 5.0 μg/mm$^2$, the sample pad may be peeled at the time of cutting in the production of the device or housing in a package or uneven coloring of a detection line may occur, and thus it goes to waste. When the surfactant is used within a range of 0.10 to 5.0 μg/mm$^2$, the surfactant works in cooperation with the high flow rate properties of the membrane of the chromatography medium, and thus, a prozone phenomenon can be further suppressed.

As the membrane to be used for the chromatography medium of the present invention, a membrane having a fast flow speed (development rate) is used. A membrane having a high flow rate (a time required for sucking up water by 4 cm (sec/40 mm)) (HFR) of 75 (sec/40 mm) or less can be used, and preferred is a membrane having an HFR of 60 (sec/40 mm) or less, and particularly preferred is a membrane having an HFR of 45 (sec/40 mm) or less.

In the case of a membrane having a high flow rate (HFR) (a time required for sucking up water by 4 cm (sec/40 mm)) exceeding 75 (sec/40 mm) and has a slow development rate, a complex of a substance to be detected (an antigen or the like) and a labeling substance cannot promptly migrate in the membrane as compared with the substance to be detected (the antigen or the like), and therefore, in a test for an analyte in which the substance to be detected (the antigen or the like) is present in a large excess amount, a prozone phenomenon cannot be suppressed.

In consideration of the measurement time required for detection, accuracy, and the like, designing can be arbitrarily performed up to the HFR of about 20 (sec/40 mm). Preferred is a membrane having an HFR of 30 (sec/40 mm) or more, and particularly preferred is a membrane having an HFR of 36 (sec/40 mm) or more.

With respect to the properties of this membrane support, a material capable of absorbing a sample analyte and allowing the sample analyte to migrate therein by a capillary phenomenon or the like is recommended. This migration phenomenon needs to be examined from the viewpoint of the properties of a material constituting the membrane support, and the structure that the membrane is a porous material which exhibits the capillary phenomenon. The designing of the structure of this membrane support needs to be examined from the viewpoint of both material and structure.

In any case, it is not particularly limited as long as it is a membrane having a fast flow speed (development rate). It is preferred to select a support material having a high flow rate (HFR) of 75 (sec/40 mm) or less particularly for achieving an object to suppress/exclude a prozone phenomenon.

For example, the membrane is produced from a material such as a natural material such as nitrocellulose, cellulose acetate, or cellulose, a synthetic polymer such as nylon, polyether sulfone, polyvinyl alcohol, polyester, or polyolefin, or an inorganic fiber such as glass fiber or carbon fiber, and may be composed of a mixed fiber. The state of use of the membrane support can be, for example, selected from membrane supports in an arbitrary form such as a fiber, a woven fabric, a nonwoven fabric, a cloth, a membrane, a paper, an open-cell sponge, a sheet, a foam, or a pad, however, the designing can be performed in consideration of the performance of HFR.

The dimension of this membrane support is not particularly limited, and a general membrane support to be applied to this type of product can be utilized, however, a membrane support having a width of 3 to 10 mm, a length of 2 to 6 cm, and a thickness of 100 to 150 μm is exemplified as a standard membrane support. The membrane is porous, and therefore may be lined by bonding a water-impermeable film of polyester, polyethylene, or the like thereto, or formed by stacking a nitrocellulose membrane on a water-impermeable plastic film of polyester, polyethylene, or the like in advance. The thickness of this water-impermeable film is not particularly limited, however, a film having a thickness of about 100 μm is preferred from the viewpoint of handleability.

In the immunochromatography device of the present invention, as the gold nanoparticles to be used as the labeling substance, red gold nanoparticles and/or blue gold nanoparticles having an average particle diameter of 10 to 60 nm, preferably about 20 to 60 nm are preferred. Of course, it is also possible to use noble metal particles of platinum, silver, rhodium, palladium, germanium, or the like, or metal nanoparticles of titanium, zinc, iron, or the like having an average particle diameter of 10 to 60 nm, preferably about 20 to 60 nm.

Such metal nanoparticles are in a dispersed state, and for example, an antibody- or antigen-sensitized colloidal metal, sensitized colloidal gold, sensitized colloidal platinum-gold, sensitized colloidal gold-silver, colloidal iron, and the like are exemplified, however, colloidal gold is most recommended since it is easily obtained and handled. The average particle diameter can be determined based on a commonly used measurement method in which the particle size distribution of colloids is measured by a dynamic light scattering particle size distribution analyzer, and thereafter, the average particle diameter is determined.

Examples of the test sample (analyte) in the present invention include mainly biological samples, and specific examples thereof not only include blood, serum, plasma, urine, saliva, sweat, spinal fluid, tear, amniotic fluid, nipple discharge fluid, nasal discharge, sputum, nasal aspirate, pharyngeal swab, bronchoalveolar lavage fluid, exudate from the skin, rectal swab, feces, and extracts from tissues or cells, but also include samples such as food extracts, tap water, sewage or waste water, and culture solutions, and it is not particularly limited. The present invention is particularly useful in the case where a substance to be detected (an antigen or the like) is contained in a large excess amount in such an analyte, and a test can be simply and accurately performed without causing a prozone phenomenon.

The detection target of the present invention may be any and is not particularly limited as long as a substance which specifically binds to the detection target, for example, specifically binds to the detection target as in the case of an antigen-antibody reaction exists or can be produced. The detection target may be a complete antigen having antigenicity itself, or may be a hapten (incomplete antigen) which does not have antigenicity itself, but will have antigenicity by being formed into a chemically modified substance. The detection target may be any as long as the substance which specifically binds to such a detection target exists or can be produced, and a monoclonal antibody or a polyclonal antibody can be used.

Examples of the detection target of the present invention include hormones such as peptide hormones (growth hormone (GH)), adrenocorticotropic hormone (ACTH), melanocyte-stimulating hormone (MSH), prolactin, thyroid-stimulating hormone (TSH), luteinizing hormone (LH), follicle-stimulating hormone (FSH), pituitary hormone, calcium metabolism-regulating hormone, pancreatic hormone, gastrointestinal hormone, vasoactive hormone, human chorionic gonadotrophin (hCG), estrogen such as estrone, natural or synthetic luteinizing hormone such as progesterone, androgenic hormone such as testosterone, adrenocortical hormone such as cortisol, and thyroid hormone such as diiodo thyronine, cancer-specific substances such as prostatic acid phosphatase (PAP), prostate-specific antigen (PSA), alkaline phosphatase, transaminase, trypsin, pepsinogen, α-fetoprotein (AFP), and carcinoembryonic antigen (CEA), serum protein components such as immunoglobulin G (IgG), rheumatoid factor, serotonin, urokinase, ferritin, Substance P, fecal occult blood, syphilis antibody, influenza virus, adenovirus, rotavirus, *Mycoplasma*, HBs antigen, HBs antibody, *Chlamydia* antigen, group A β-hemolytic *streptococcus* antigen, cholesterol, bile acid, other steroids such as cardiotonic steroid and sapogenin, epinephrine, dopamine, bioactive alkaloids, amino group-containing psychotropic drugs, low molecular weight peptides such as TRH, prostaglandins, vitamins, antibiotics such as penicillin, other components in the body, drugs administered to the body, and metabolites thereof.

Preferred examples of the detection target include particularly luteinizing hormone (LH), follicle-stimulating hormone (FSH), human chorionic gonadotrophin (hCG), estrogen such as estrone, natural or synthetic luteinizing hormone such as progesterone, and as the sample (analyte) containing the detection target of the present invention, for example, urine, blood, or the like is used.

It is preferred that a buffer or a surfactant, particularly a nonionic surfactant is included in a labeling substance solution or the like for immunochromatography of the present invention.

The buffer to be included is not particularly limited as long as it has an action (buffering action) that a critical effect is not caused even if the concentration is changed by the addition of a sample or the evaporation or dilution of a sample or contamination with some foreign matter from the outside.

In the present invention, examples of the buffer include an acetate buffer solution (acetic acid+sodium acetate), a phosphate buffer solution (phosphoric acid+sodium phosphate), a citrate buffer solution (citric acid+sodium citrate), a borate buffer solution, a Tris-HCl buffer solution (Tris(hydroxylmethyl)aminomethane+hydrochloric acid), a TE buffer solution (Tris+ethylenediaminetetraacetic acid), a TAE buffer solution (Tris+acetic acid+ethylenediaminetetraacetic acid), a TBE buffer solution (Tris+boric acid+ethylenediaminetetraacetic acid), and a HEPES buffer solution (2-[4-(2-hydroxyethyl)-1-piperazinyl]ethanesulfonic acid).

Preferred is a HEPES buffer solution, a phosphate buffer solution, an acetate buffer solution, a Tris-HCl buffer solution, or the like, and more preferred is a phosphate buffer solution or a HEPES buffer solution. Further, it is also possible to blend and use another buffer as long as an adverse effect is not exerted.

The concentration of the buffer to be used in the present invention is preferably in a range of 10 to 500 mM, more preferably in a range of 10 to 300 mM, further more preferably in a range of 30 to 100 mM. When the concentration is lower than 10 mM, the buffering action is insufficient, and also the suppression of the deposition of protein components or the suppression of aggregation of labeling particles is also insufficient. When the concentration exceeds 500 mM, it is more than necessary, and therefore it is not economical and goes to waste. Further, as the buffer solution, it is most preferred to prepare a buffer solution having a pH in a range of 7.1 to 9.8.

In the respective parts of the immunochromatography device of the present invention, particularly to the membrane of the chromatography medium, it is possible and effective to use one type or two or more types of known additives capable of suppressing side reactions based on biological affinity or suppressing non-specific reactions, for example, proteins (for example, bovine serum albumin, gelatin, etc.), high molecular weight compounds (for example, polyethylene glycol, methyl cellulose, polyvinylpyrrolidone, polyvinyl alcohol, dextran, etc.), ionic surfactants or polyanions (for example, dextran sulfate, heparin, polystyrene sulfonic acid, chondroitin sulfate, etc.), or antimicrobial agents, etc. for promoting an antigen-antibody reaction or suppressing non-specific reactions by adding and retaining such additives therein, and such additives do not interfere at all.

Further, it is also possible and effective to retain one type or two or more types of these proteins, high molecular weight compounds, ionic surfactants or polyanions, or antimicrobial agents, etc. for promoting an antigen-antibody reaction or suppressing non-specific reactions on a migration path of a mobile phase on the chromatography medium constituting a stationary phase, and such additives do not interfere at all.

As for the content of the above additives to be included in the sample pad (SP) or in the sample pad (SP) and the conjugation pad (CP) in the immunochromatography device of the present invention, the content per unit area when an aqueous solution in a concentration range of 0.01 to 20 mass %, preferably in a concentration range of 0.1 to 10 mass %, more preferably in a concentration range of 0.5 to 5 mass % is applied or impregnated, and then dried is set to 0.10 to 10.0 $\mu g/mm^2$, preferably 0.15 to 5.0 $\mu g/mm^2$, particularly preferably 0.20 to 1.0 $\mu g/mm^2$.

When the content is less than 0.10 $\mu g/mm^2$, non-specific reactions cannot be suppressed, and an accurate determination cannot be made. On the other hand, when the content exceeds 10.0 $\mu g/mm^2$, it is more than necessary, and therefore it is not economical and goes to waste. When the content per unit area is within a range of 0.10 to 10.0 $\mu g/mm^2$, such an additive works in cooperation with the high flow rate properties of the membrane of the chromatography medium, and thus, a prozone phenomenon can be further suppressed.

When the labeling substance solution for immunochromatography of the present invention is retained in the solid phase, as a protection stabilization substance or a dissolution enhancing substance to be included in the labeling substance solution, a saccharide, that is, a monosaccharide, a disaccharide, a trisaccharide, an oligosaccharide, or a polysaccharide can be used.

Examples of the monosaccharide include glucose, galactose, xylose, and fructose, examples of the disaccharide include trehalose, sucrose, lactose, and maltose, examples of the trisaccharide or the oligosaccharide include raffinose, and examples of the polysaccharide include gluconic acid and dextran. It is acceptable to use one type or two or more types in admixture among these.

Further, in the case of providing the labeling substance retaining part of the present invention in a part of a region of the immunochromatography device, it is preferably supported or retained or formed therein by applying, adsorbing, or impregnating a composition containing a labeling substance protection stabilization reagent obtained by subjecting a labeling substance to a protection treatment with an alkylene glycol having at least one mercapto group with a molecular weight of 1000 to 30000 and/or a derivative thereof (a protective reagent), and according to need, further mixing arginine and casein (a stabilization reagent) therein, in a region between an end portion of the sample addition part and the determination part, followed by drying by any of a variety of drying means (aeration drying, vacuum drying, natural drying, lyophilization, etc.).

As a method for providing a part containing the labeling substance solution for immunochromatography of the present invention or another reagent composition, for example, a mode in which the labeling substance solution for immunochromatography is supported or retained in a glass fiber pad (a labeling substance retaining member) in the immunochromatography device by a method in which the labeling substance solution for immunochromatography is applied or impregnated in the glass fiber pad, followed by drying by any of a variety of drying means can be adopted.

In the case of performing the immunochromatography detection method of the present invention, a mode in which an analyte is directly added dropwise to the sample addition part, or the sample addition part is immersed in an analyte is adopted. However, in the case where the analyte is in the form of a solid such as sputum, it is also possible to use an analyte dilution solution.

This analyte dilution solution can also be used as a developing solution, however, in general, water is used as a solvent, and thereto, a buffer solution, a salt, and a nonionic surfactant, and further, one type or two or more types of proteins, high molecular weight compounds (PVP, etc.), ionic surfactants or polyanions, or antimicrobial agents, chelating agents, etc. for promoting an antigen-antibody reaction or suppressing non-specific reactions described above are added.

The addition order is not particularly limited, and it is acceptable to add the components simultaneously. In the case where it is used as a developing solution, a mixture obtained by mixing a detection sample and the developing solution in advance can be supplied and added dropwise on the sample pad (sample addition part) to effect development, or a sample is supplied and added dropwise on the sample pad first, and thereafter, the developing solution may be supplied and added dropwise on the sample pad to effect development. In the case where it is used as a sample dilution solution, a sample is adjusted or diluted with the sample dilution solution so as to make the concentration thereof suitable for measurement, and then, the solution can be used by being supplied and added dropwise on the sample pad.

The immunochromatography device and specifications will be described below.

An immunochromatography device or an immunochromatography kit (1) is constituted by a sample addition part (2) (also referred to as "sample pad"), a labeling substance retaining part (3) (also referred to as "conjugate pad"), a chromatography medium (4), a determination part (5), further, a control part (8) as needed, an absorption part (6) (also referred to as "development rate control part"), and a backing sheet (7). The structures, specifications, and modes of these respective parts are as follows.

1) With reference to FIG. 1, the sample addition part (2) ("sample pad") is constituted by a porous sheet having properties such that it rapidly absorbs a sample, but has a low ability to retain the sample so that the sample promptly migrates to a reaction part. Examples of the porous sheet include a cellulose filter paper, a glass fiber filter paper, polyurethane, polyacetate, cellulose acetate, rayon, nylon, and a cotton cloth. As the porous sheet of the present invention, a glass fiber filter paper and rayon are preferably used. In the present invention, in order to suppress/exclude a prozone phenomenon, it is possible to adopt a mode in which a reagent composition for immunochromatography containing a nonionic and hydrophilic surfactant having an HLB of 13 to 18 and according to need, a buffer solution is supported by a means such that the composition is impregnated into at least the sample pad (2) in advance, and thereafter dried or the like.

As the nonionic surfactant to be retained in the sample pad of the immunochromatography kit of the present invention, a nonionic surfactant having an HLB (Hydrophile-Lipophile Balance=the weight percentage of hydrophilic groups× 0.2=0 to 20) of 13 to 18 can be used.

For example, polyoxyalkylene alkyl ethers, polyoxyethylene alkyl ethers (for example, registered trademark "Brij" series), polyoxyethylene/polyoxypropylene alkyl ethers (for example, trade name: NP-40, manufactured by Nacalai Tesque, Inc.), polyoxyethylene aryl ethers, polyoxyethylene sorbitan fatty acid esters (for example, trade name "Tween" series), polyoxyethylene p-t-octylphenyl ethers (for example, trade name "Triton" series), for example, polyoxyethylene (10)-p-t-octylphenyl ether (Triton X-100 (trade name), HLB=13.7), polyoxyethylene p-t-nonylphenyl ethers (for example, trade name: "Triton N" series), polyoxyalkylene aryl ethers, polyoxyalkylene polycyclic phenyl ethers, polyoxyethylene alkyl amine ethers, polyoxyethylated hydrogenated castor oils, and the like, each having an HLB value of 13 to 18 can be exemplified. Further, it is also possible to use these nonionic surfactants in admixture as long as an adverse effect is not exerted.

2) In the labeling substance retaining part (3), a labeling reagent in which a reagent component is labeled with a labeling component is supported or retained. As the labeling component, colloidal metal particles such as colloidal gold particles and colloidal silver particles, colored latex particles obtained by staining a synthetic polymer synthesized by (co)polymerizing any of a variety of monomers, an enzyme, a fluorescent compound, and others can be used. The reagent component is a particle or a molecule having an ability to recognize an analyte, and is preferably a monoclonal antibody or a polyclonal antibody, or a fragment thereof (a second reagent).

Further, in the present invention, in order to suppress/exclude a prozone phenomenon, it is preferred to adopt a mode in which a reagent composition for immunochromatography containing a nonionic and hydrophilic surfactant having an HLB of 13 to 18 and according to need, a buffer solution is supported by a means such that the composition is impregnated not only into the sample pad (2), but also into the labeling substance retaining part (3) in advance, and thereafter dried or the like.

3) The chromatography medium (4) is configured such that a determination part (also referred to as "detection part") (5) is formed on a membrane support. The membrane support is not particularly limited as long as it can absorb a sample analyte and allow the sample analyte to migrate therein by a capillary phenomenon, and has a fast flow speed (development rate). A high flow rate HFR of 75 (sec/40 mm) or less, preferably an HFR of 20 to 60 (sec/40 mm) is preferred for suppressing/excluding a prozone phenomenon.

The HFR is more preferably from 30 to 60 (sec/40 mm), and particularly preferably from 36 to 60 (sec/40 mm). For example, it is selected from the group consisting of nitrocellulose, cellulose acetate, nylon, polyether sulfone, polyvinyl alcohol, polyester, glass fiber, polyolefin, cellulose, and an artificial polymer composed of a mixed fiber thereof. It is composed of an arbitrary material such as a fiber, a woven cloth, a nonwoven cloth, a cloth, a membrane, or the like thereof.

4) In the determination part (5), a monoclonal antibody or a polyclonal antibody, or a fragment thereof (a first reagent) is supported and fixed onto a nitrocellulose sheet.

As for the reagent component (first reagent) to be used in this determination part (5) and the reagent component (second reagent) to be used in the labeling reagent, one or both of them may be a monoclonal antibody or may be a polyclonal antibody, however, in the case where the production cost and the stable supply of the antibody while maintaining the specificity are considered, it is preferred that at least one of them is a polyclonal antibody.

Further, the reagent component (second reagent) to be used in the labeling reagent is more preferably a monoclonal antibody having high specificity from the viewpoint of measurement sensitivity or the like. However, it is most preferred to use a monoclonal antibody as both of the first reagent and the second reagent from the viewpoint of reaction accuracy and efficiency.

The monoclonal antibody, the polyclonal antibody, and the fragment thereof are known and available, and can be prepared by a known method. Examples of an animal species that produces the antibody include a human being, a mouse, a rat, a rabbit, and a goat. The immunoglobulin may be any of IgG, IgM, IgA, IgE, and IgD.

The monoclonal antibody is obtained according to a conventional method as follows. The spleen cells and myeloma cells of a mouse immunized with an antigen are fused, and a hybridoma which produces a desired antibody is selected, and a monoclonal antibody produced from this hybridoma is obtained. For example, the method of Kohler and Milstein (Nature, 256 (1975), 495-497) can be referred to.

The polyclonal antibody is obtained by separating a desired antibody from an antiserum obtained by immunizing an antibody-producing animal (for example, a human being, a mouse, a rat, a rabbit, a goat, a horse, etc.) with an antigen according to a conventional method.

5) In the absorption part (6), a filter paper composed of glass fiber, cellulose fiber, or the like which is a material having an ability to rapidly absorb an excess amount of a sample is widely used, however, it is more preferred to use a material further having an ability to retain the absorbed liquid so as not to flow back. A particularly preferred mode is as disclosed in (JP-A-2012-189346).

6) The backing sheet (7) is a base material. By applying an adhesive to one surface or bonding an adhesive tape to one surface, the surface has adhesiveness, and on the adhesive surface, the sample addition part (2), the labeling substance retaining part (3), the chromatography medium (4) having the detection part (5), and the absorption part (6) are provided such that these members are in close contact partially or entirely with the adhesive surface. The backing sheet (7) is not particularly limited as the base material as long as it becomes impermeable to a sample liquid and also is impermeable to moisture by the adhesive.

Hereinafter, the effectiveness of the present invention will be described with reference to Examples of the respective specifications and embodiments, however, the present invention is not limited thereto.

EXAMPLES

Hereinafter, the significance of the present invention will be described with reference to Examples and Comparative Examples. The specification of the implementation is as follows.

Example 1

1. Formation of Determination Part on Chromatography Medium

To a membrane composed of cellulose with a size of 2.5×25 cm, an anti-LH (luteinizing hormone) monoclonal antibody at a concentration of 1.8 mg/mL diluted with a phosphate buffer solution (pH 7.5) containing 5 mass % isopropyl alcohol was applied using an antibody applicator (manufactured by BioDot, Inc.), followed by drying, whereby a determination part was formed on a chromatography medium.

2. Preparation of Labeling Reagent Solution

To 0.9 mL of a colloidal gold suspension (manufactured by Tanaka Kikinzoku Kogyo K.K.: 40 nm), 0.1 mL of a phosphate buffer solution (pH 7.5) was added and mixed, and 0.05 mL of a solution of an anti-LH monoclonal antibody at 50 µg/mL diluted with a phosphate buffer solution (pH 7.5) was added thereto, and the resulting mixture was left to stand at room temperature for 10 minutes. Then, 0.1 mL of a Tris buffer solution (pH 7.5) containing 0.01 mass % PEG-SH (manufactured by NOF Corporation, trade name: SUNBRIGHT ME-200SH, molecular weight: 20000) was added thereto, and the resulting mixture was thoroughly stirred, and then centrifuged at 8000×g for 15 minutes. After removing the supernatant, 1 mL of a phosphate buffer solution (pH 7.5) was added thereto. The colloidal labeling reagent was well dispersed using an ultrasonic homogenizer, and then, the dispersion was centrifuged at 8000×g for 15 minutes. After removing the supernatant, 0.15 mL of the phosphate buffer solution was added to the residue, and the residue was well dispersed using an ultrasonic homogenizer, whereby a labeling reagent solution was prepared.

3. Preparation of Sample Pad (Sample Addition Part)

To a rayon pad with a size of 3.0×25 cm, a 2 mass % aqueous solution of Tween 20 (manufactured by Sigma-Aldrich Corporation, trade name: Tween (registered trademark) 20, HLB (Hydrophile-Lipophile Balance) value: 16.7) as a nonionic surfactant was uniformly applied so that the content per unit area was as shown in the table, followed by drying in a vacuum dryer, whereby a sample pad was prepared.

4. Preparation of Chromatography Medium

The labeling reagent solution prepared above (0.22 mL) was added and mixed in 0.78 mL of a 10% aqueous solution of trehalose, and the resulting mixture was uniformly added to a glass fiber pad with a size of 1.6×25 cm, followed by drying in a vacuum dryer, whereby a labeling reagent retaining member was prepared. Subsequently, to a base material composed of a backing sheet, the nitrocellulose membrane having the determination part formed thereon in the above, the labeling reagent retaining member, the sample pad prepared in the above, and an absorption pad of cellulose fiber for absorbing a developed sample, a labeling reagent, and the like were bonded. Finally, the resulting material was cut to a width of 5 mm by a cutter, whereby a chromatography medium was prepared.

5. Measurement

By using the chromatography medium prepared in the above 4, a detection test for LH which is a substance to be detected was performed. As for a negative analyte, 150 µL of male urine containing LH at 0 mIU/mL was used as a negative analyte sample. Further, in Tables 1 to 3, as a positive analyte sample, 150 µL of a sample diluted with male urine containing LH at a concentration of 40 mIU/mL was used, and in addition, in Table 4, as a positive analyte sample, 150 µL of a sample diluted with male urine containing LH at a concentration of $20 \times 10^6$ mIU/mL was used, and the test was performed. In Table 5, samples containing LH in a concentration range of 0 to $2 \times 10^7$ mIU/mL were used, and further membranes having am HFR of 45 or 75 were used, and the test was performed. Each of the negative analyte sample and the positive analyte samples was added and developed on the sample pad of a test piece for immunochromatography in an amount of 150 µL, and after 15 minutes, a visual determination was made.

Regarding flow: When the sample liquid was developed on the membrane after the measurement was started, the development of the liquid and the development of the red color of the labeling reagent were visually confirmed.

A case where the labeling reagent was developed at the same rate or substantially the same rate as the developed liquid was evaluated as "A", a case where the labeling reagent was developed a little later than the developed liquid was evaluated as "B", and a case where the labeling reagent was developed later than the developed liquid was evaluated as "C".

Regarding Sensitivity:

A case where a red line in the determination part can be confirmed was evaluated as "A", a case where a red line can be confirmed, but the color is very light was evaluated as "B", and a case where a red line cannot be confirmed was evaluated as "C".

Visual Determination Criteria:

A case where a red line in the determination part can be confirmed was evaluated as "+", a case where a red line can be clearly confirmed was evaluated as "++", a case where a red line can be more strongly and clearly confirmed was evaluated as "+++", a case where a red line can be confirmed, but the color is very light was evaluated as "±", and a case where a red line cannot be confirmed was evaluated as "−".

The test results are shown in the tables.

Incidentally, the nonionic surfactants used in Tables 1 to 4 are as follows.

[Regarding Nonionic Surfactant]

MN-811: manufactured by NOF Corporation, trade name: NONION MN-811

Triton X-100: manufactured by Sigma-Aldrich Corporation, trade name: Triton X-100

Brij 35: registered trademark of ICI Americas, Inc., trade name: Brij 35

Tween 20: trade name of ICI Americas, Inc.: polyoxyethylene (20) sorbitan monolaurate NP-40: manufactured by Nacalai Tesque, Inc., trade name: Nonidet P-40

In the chromatography medium prepared in the above 4, in place of Tween 20 which is the nonionic surfactant to be added to the sample pad (SP), any of a variety of nonionic surfactants having a different HLB value was used, and a detection test for LH which is a substance to be detected was performed, and evaluation and examination for the nonionic surfactants clue to the difference in the HLB value were performed. The content of the nonionic surfactant to be added to the sample pad (SP) is 0.2 µg/mm$^2$. As a negative analyte, 150 µL of a sample diluted with male urine containing LH at 0 mIU/mL was used, and as a positive analyte, 150 µL of a sample diluted with male urine containing LH at a concentration of 40 mIU/mL was used, and the test was performed. The test results are shown in Table 1.

[Table 1]

TABLE 1

| Surfactant | MN-811 | Triton X-100 | Brij 35 | Tween 20 | NP-40 |
|---|---|---|---|---|---|
| HLB value | 9.3 | 13.7 | 15.3 | 16.7 | 17.7 |
| Flow | C | A | A | A | A |

TABLE 1-continued

| Surfactant | MN-811 | Triton X-100 | Brij 35 | Tween 20 | NP-40 |
|---|---|---|---|---|---|
| Sensitivity | B | C | A | A | C |
| Content (μg/mm$^2$) | 0.2 | 0.2 | 0.2 | 0.2 | 0.2 |

As apparent from the results shown in Table 1, in the case where a nonionic and hydrophilic surfactant having an HLB value of 13 to 18 was used, the complex of LH and the labeling substance was developed at a flow rate from the sample pad to the absorption part which is the same or substantially the same as that of the developed liquid, and therefore, the flow is favorable. Further, it was found that in the case where a nonionic and hydrophilic surfactant having an HLB value of 14 to 17 was used, the sensitivity in the detection line is also favorable. Brij 35 and Tween 20 were preferred from the viewpoint of both flow and sensitivity, and in particular, Tween 20 was preferred also from the viewpoint of storage stability.

A detection test for LH which is a substance to be detected was performed by the same procedure and mode as described above except that in the chromatography medium prepared in the above 4, Tween 20 or Brij 35 was used as the nonionic surfactant to be added only to the sample pad (SP), and the content thereof was changed, and evaluation and examination due to the difference in the content of the nonionic surfactant were performed. When the evaluation was performed for the negative and positive analytes using the test device, as a negative analyte 150 μL, of a sample diluted with male urine containing LH at 0 mIU/mL was used, and as a positive analyte, 150 μL of a sample diluted with male urine containing LH at a concentration of 40 mIU/mL was used, and the test was performed. Then, a determination was made according to the same visual determination criteria. The test results are shown in Table 2.

[Table 2]

TABLE 2

| Nonionic surfactant | Tween 20 | | | | | | | |
|---|---|---|---|---|---|---|---|---|
| Content (μg/mm$^2$) | 0.05 | 0.10 | 0.15 | 0.20 | 0.30 | 0.40 | 0.50 | 0.60 |
| Flow | C | B | B | A | A | A | A | A |
| Sensitivity | A | A | A | A | A | A | A | A |
| Nonionic surfactant | Brij 35 | | | | | | | |
| Content (μg/mm$^2$) | 0.05 | 0.10 | 0.15 | 0.20 | 0.30 | 0.40 | 0.50 | 0.60 |
| Flow | C | B | B | A | A | A | A | A |
| Sensitivity | A | A | A | A | A | A | A | A |

As apparent from the results shown in Table 2, it was found that when the content of Tween 20 or Brij 35 as the nonionic surfactant to be added only to the sample pad (SP) was within a range of 0.20 to 0.60 μg/mm$^2$, both flow and sensitivity are favorable. In the case where the content is too large, damage such as peeling may sometimes occur when the device is produced or the device is housed in a package, or due to an uneven dried state, uneven coloring of the detection line may sometimes be caused.

A preparation was performed by the same procedure and mode as described above except that in the chromatography medium prepared in the above 4, Tween 20 which is a nonionic surfactant was added to both of the sample pad (SP) and the conjugation pad (CP). Then, by changing the content of Tween 20, a detection test for LH which is a substance to be detected was performed, and evaluation and examination due to the difference in the content were performed. When the evaluation was performed for the negative and positive analytes using the test device, as a negative analyte, 150 μL of a sample diluted with male urine containing LH at 0 mIU/mL was used, and as a positive analyte, 150 μL of a sample diluted with male urine containing LH at a concentration of 40 mIU/mL was used, and the test was performed. The test results are shown in Table 3.

[Table 3]

TABLE 3

| Nonionic surfactant | Tween 20 | | | | | | | | | | |
|---|---|---|---|---|---|---|---|---|---|---|---|
| CP | 0.0005 | | 0.001 | | 0.003 | | 0.004 | | 0.005 | 0.025 | 0.005 |
| SP | 0.100 | 0.150 | 0.100 | 0.150 | 0.100 | 0.150 | 0.100 | 0.150 | 0.100 | 0.200 | 0.300 |
| Flow | C | C | C | C | C | A | B | A | A | A | A |
| Sensitivity | A | A | A | A | A | A | A | A | A | A | A |

As apparent from the results shown in Table 3, it is found that although Tween 20 as the nonionic surfactant may be added only to the sample pad (SP), it is more preferred to add the nonionic surfactant to both of the sample pad (SP) and the conjugation pad (CP). It was found that rather than by adding the nonionic surfactant only to the sample pad (SP), by adding the nonionic surfactant to both of the sample pad (SP) and the conjugation pad (CP), even if the total content of the nonionic surfactant is small, it functions favorably in terms of both flow and sensitivity.

Evaluation and examination were performed for an effect of suppressing a prozone phenomenon due to the difference in the properties of the flow rate (High Flow Rate: a time required for sucking up water by 4 cm (sec/40 mm)) of the membrane to be used in the chromatography medium prepared in the above 4. As the nonionic surfactant to be added only to the sample pad (SP), Tweet 20 or Brij 35 was used, and the content thereof was set to 0.2 μg/mm$^2$. A test was performed by the same operation procedure and mode as described above except that as a positive analyte, 150 μL of a sample diluted with male urine containing LH at a concentration of 20×10$^6$ mIU/mL was used. Then, a determination was made according to the same visual determination criteria. The determination results are shown in Table 4.

[Table 4]

TABLE 4

| Nonionic surfactant | Tween 20 | | | | | |
|---|---|---|---|---|---|---|
| High Flow Rate | 36 | 45 | 60 | 75 | 120 | 180 |
| Flow | A | A | A | A | A | A |
| Sensitivity | +++ | +++ | + | ± | − | − |

TABLE 4-continued

| Nonionic surfactant | Brij 35 | | | | | |
|---|---|---|---|---|---|---|
| High Flow Rate | 36 | 45 | 60 | 75 | 120 | 180 |
| Flow | A | A | A | A | A | A |
| Sensitivity | +++ | +++ | + | ± | − | − |

As apparent from the results shown in Table 4, an effect of suppressing a prozone phenomenon was obtained when the high flow rate of the membrane was 75 (sec/40 mm) or less.

In the following, evaluation and examination for an effect of suppressing a prozone phenomenon with respect to the concentration range of a substance to be detected were performed by measuring the coloring strength (absorbance) using samples in which the concentration of the substance to be detected was within a concentration range of 0 to $2\times10^7$ mIU/mL, and also using membranes having an HFR of 45 or 75.

In the chromatography medium prepared in the above 4, with respect to the properties of the flow rate (HFR: sec/40 mm) of the membrane to be used, two types (HFR45 and HFR75) were used. In the case of HFR45, the measurement was performed for a case where a nonionic surfactant (Tween 20, 0.4 μg/mm$^2$) was added only to the sample pad (SP), and a case where a nonionic surfactant (Tweet 20, 0.2 μg/mm$^2$) was added to the sample pad (SP) and a nonionic surfactant (Tween 20, 0.2 μg/mm$^2$) was also added to the conjugation pad (CP). In the case of HFR75, a nonionic surfactant (Tween 20, 0.4 μg/mm$^2$) was added only to the sample pad (SP), and the measurement was performed.

A test was performed by the same operation procedure and mode as described above except that as a positive analyte, 150 μL of samples diluted with male urine containing LH at a concentration of 3 to $2\times10^7$ mIU/mL were used and also the test was performed under the above-mentioned conditions, and evaluation and examination for an effect of suppressing a prozone phenomenon were performed. Then, a determination was made according to the same visual determination criteria. The determination results are shown in Table 5.

When the coloring strength (absorbance) is less than 10, a visual determination cannot be made, and when the coloring strength (absorbance) is 10 or more, a visual determination can be made.

TABLE 5

| mIU/mL | HF45 (CP + SP) | HF45 (SP) | HF75 | |
|---|---|---|---|---|
| 0 | 0 | 0 | 0 | |
| 3 | 0 | 0 | 0 | |
| 20 | 15 | 17.5 | 8.3 | |
| 50 | 34 | 39.5 | 26.9 | ↓ |
| 1000 | 259.6 | 232.1 | 275.3 | |
| 10000 | 352.1 | 300 | 385.1 | |
| 100000 | 298.5 | 450.7 | 100 | absorbance |
| 250000 | 288.2 | 386.6 | 75 | |
| 500000 | 294.2 | 218.4 | 22 | |
| 1000000 | 197.9 | 108.8 | 8.4 | ↑ |
| 2000000 | 120.5 | 57.4 | 0 | |
| 5000000 | 52.7 | 27.6 | 0 | |
| 10000000 | 23.5 | 11.3 | 0 | |
| 20000000 | 6.1 | 4.6 | 0 | |

As apparent from the results shown in Table 5, it is found that in the present invention, an effect of suppressing/excluding a prozone phenomenon is quite significantly exhibited in an extremely wide concentration range of the amount of the substance to be detected.

A graph obtained by graphing the data in Table 5 is shown in FIG. 2. When viewing the graph, the effect of suppressing/excluding prozone phenomenon exhibited by the present invention is clearer. It is clearly found that in the case of HFR45, a visual determination can be made when the concentration of the substance to be detected is within a range of 20 to $1\times10^7$ mIU/mL, and in the case of HFR75, a visual determination can be made when the concentration of the substance to be detected is within a range of 50 to $5\times10^5$ mIU/mL.

From these results, it is found that the concentration zone of the substance to be detected in which a visual determination can be made expands in both zones of the low concentration and the high concentration in the case of HFR45 having a fast flow speed (development rate) of the membrane as compared with the case of HFR75 having a slow flow speed (development rate). That is, the results support that for a high concentration analyte, an effect of suppressing/excluding a prozone phenomenon is extremely significantly exhibited, and also for a low concentration analyte, the effect is exhibited without reducing coloration.

In this manner, the present inventors found that the immunochromatography kit as shown in FIG. 1 of the present invention can achieve a particularly significant function that it can suppress a prozone phenomenon in an extremely wide concentration range of a substance to be detected, and also it can obtain a sufficient coloring strength without reducing coloration even when the concentration of a substance to be detected is low by retaining a specific nonionic surfactant in a dry state at least in a sample addition part (sample pad) and using a membrane having a fast flow speed (development rate) as a membrane to be used for the chromatography medium.

From these results, it was revealed that when a detection target in an analyte is tested by an immunochromatography method, according to the present invention in which a nonionic surfactant having an HLB value of 13 to 18, more preferably a nonionic surfactant having art HLB value of 14 to 17 is retained at least in a sample addition part (sample pad) and a membrane having a high flow rate of 75 (sec/40 mm) or less is used as a membrane to be used for the chromatography medium, by making the flow of the analyte, fast, a coloring antibody (a complex of a detection target (antigen) and a labeling substance) can reach before the detection target (antigen) covers the detection antibody on the membrane, and therefore, even if the detection target (antigen) is present in the analyte in a large excess amount, a remarkable effect that a prozone phenomenon is significantly suppressed, the development rate is fast, and an accurate determination with a high S/N ratio can be made is exhibited.

INDUSTRIAL APPLICABILITY

The present invention has excellent advantages that it can be used for immunological diagnostic method and device, each of which does not need an analyte extract or the like such as urine or blood, and moreover, is capable of rapidly and simply performing a test or a diagnosis by suppressing/excluding a prozone phenomenon even in a system in which a detection target (an antigen or the like) is present in an analyte in a large excess amount, and therefore has industrial applicability that not only hospitals or clinics, but also individuals who do not have a special skill can perform a clinical test rapidly with high sensitivity, which leads to early diagnosis or treatment of diseases.

Further, an analyte in a wide range from a low concentration to a high concentration can be handled, and also a diluent or the like is not needed, and moreover, a prozone phenomenon does not occur, so that the determination criteria are also simple and clear, and thus, an easy and accurate immunological diagnostic method and device are provided. Due to this, not only are the handleability, the test efficiency and the test accuracy of the kit of the present invention enhanced, but also the enhancement of the test efficiency and the reduction in labor are improved, and thus, the present invention significantly contributes to the development of the industrial fields associated with testing institutions and the industrial fields associated with the medical field.

While the present invention has been described in detail with reference to specific embodiments, it is apparent to those skilled in the art that various changes and modifications can be made without departing from the spirit and scope of the present invention. The present application is based on Japanese Patent Application (Japanese Patent Application No. 2014-116036) filed on Jun. 4, 2014 and the entire contents of which are incorporated herein by reference.

REFERENCE SIGNS LIST

1 immunochromatography device (1)
2 sample addition part (2) (sample pad, SP)
3 labeling substance retaining part (3) (conjugate pad, CP),
4 membrane of chromatography medium (4)
5 detection line (5) (detection part, determination part)
6 absorption part (6) (absorption pad)
7 backing sheet (7) (omitted in drawings)
8 control line (8)

The invention claimed is:

1. An immunochromatography device for detecting a detection target in an analyte, comprising a sample addition part, a labeling substance retaining part, a chromatography medium having a detection part, and an absorption part, wherein a nonionic and hydrophilic surfactant having an Hydrophile-Lipophile Balance (HLB) value of 13 to 18 is retained at least in the sample addition part, and a membrane having a fast flow speed is used for the chromatography medium, wherein the flow speed of the membrane is 75 sec/40 mm or less.

2. The immunochromatography device according to claim 1, wherein the nonionic and hydrophilic surfactant having an HLB value of 13 to 18 is retained in both of the sample addition part and the labeling substance retaining part.

3. The immunochromatography device according to claim 1, wherein the content of the nonionic and hydrophilic surfactant is from 0.1 to 5 μg/mm$^2$ of the unit area of the sample addition part or both of the sample addition part and the labeling substance retaining part.

4. The immunochromatography device according to claim 1, wherein the labeling substance is modified with gold nanoparticles retained in a dry state in the labeling substance retaining part.

5. The immunochromatography device according to claim 4, wherein the gold nanoparticles have an average particle diameter from 20 to 60 nm.

* * * * *